(12) United States Patent
Igarashi

(10) Patent No.: US 9,313,382 B2
(45) Date of Patent: Apr. 12, 2016

(54) IMAGE PICKUP UNIT AND ENDOSCOPE DISTAL END PORTION INCLUDING THE IMAGE PICKUP UNIT

(71) Applicant: OLYMPUS CORPORATION, Tokyo (JP)

(72) Inventor: Takatoshi Igarashi, Nagano (JP)

(73) Assignee: OLYMPUS CORPORATION, Tokyo (JP)

( * ) Notice: Subject to any disclaimer, the term of this patent is extended or adjusted under 35 U.S.C. 154(b) by 398 days.

(21) Appl. No.: 13/790,884

(22) Filed: Mar. 8, 2013

(65) Prior Publication Data

US 2013/0188030 A1 Jul. 25, 2013

Related U.S. Application Data

(63) Continuation of application No. PCT/JP2011/069081, filed on Aug. 24, 2011.

(30) Foreign Application Priority Data

Sep. 10, 2010 (JP) .................................. 2010-203400

(51) Int. Cl.
*A61B 1/00* (2006.01)
*H04N 5/225* (2006.01)
(Continued)

(52) U.S. Cl.
CPC .......... *H04N 5/2254* (2013.01); *A61B 1/00064* (2013.01); *A61B 1/051* (2013.01); *H01L 27/14618* (2013.01); *H01L 27/14625* (2013.01); *A61B 1/00096* (2013.01); *H01L 2924/0002* (2013.01)

(58) Field of Classification Search
CPC ............ B41M 5/3375; A61B 1/00064; A61B 1/00096; A61B 1/051; H01L 27/14618; H01L 27/14625; H04N 5/2254
USPC .............................................................. 348/65
See application file for complete search history.

(56) References Cited

U.S. PATENT DOCUMENTS 4,819,065 A * 4/1989 Eino ................................ 348/74
4,845,555 A * 7/1989 Yabe et al. ...................... 348/72
(Continued)

FOREIGN PATENT DOCUMENTS

EP        0 978 251 A1    2/2000
JP        63-136781       6/1988
(Continued)

OTHER PUBLICATIONS

Extended Supplementary European Search Report dated Aug. 3, 2015 received from Application No. 11823413.7.

*Primary Examiner* — Shan Elahi
(74) *Attorney, Agent, or Firm* — Scully, Scott, Murphy & Presser, P.C.

(57) ABSTRACT

The application is directed to an image pickup system that includes a lens holder; an image pickup optical system that is secured by a portion of the lens holder; an image pickup device comprising a first surface and a second surface, wherein the first surface is nearer the image pickup optical system than the second surface in an optical axis direction, a light receiving sensor that receives light entering through the image pickup optical system, and a cover glass attached to the first surface of the image pickup device, wherein the cover glass comprising a fitting portion of the cover glass in an outer circumferential face of the cover glass.

9 Claims, 4 Drawing Sheets

(51) Int. Cl.
*A61B 1/05* (2006.01)
*H01L 27/146* (2006.01)

(56) References Cited

U.S. PATENT DOCUMENTS

| | | | |
|---|---|---|---|
| 6,184,923 B1* | 2/2001 | Miyazaki | 348/75 |
| 6,547,721 B1 | 4/2003 | Higuma et al. | |
| 7,585,275 B2* | 9/2009 | Kubota et al. | 600/160 |
| 7,662,094 B2* | 2/2010 | Iddan | 600/176 |
| 7,762,466 B2* | 7/2010 | Tan et al. | 235/462.42 |
| 7,976,462 B2* | 7/2011 | Wright et al. | 600/171 |
| 2003/0171649 A1 | 9/2003 | Yokoi et al. | |
| 2004/0181155 A1* | 9/2004 | Glukhovsky | 600/476 |
| 2004/0267095 A1* | 12/2004 | Miyake et al. | 600/175 |
| 2006/0132598 A1* | 6/2006 | Minami et al. | 348/76 |
| 2009/0096865 A1* | 4/2009 | McKinley | 348/45 |
| 2009/0118580 A1* | 5/2009 | Sun et al. | 600/109 |
| 2009/0216080 A1* | 8/2009 | Nakamura | 600/109 |
| 2009/0237497 A1 | 9/2009 | Iinuma et al. | |
| 2009/0303620 A1* | 12/2009 | Abe et al. | 359/819 |
| 2010/0027129 A1* | 2/2010 | Sato et al. | 359/622 |
| 2010/0225799 A1 | 9/2010 | Fujimori | |
| 2012/0075721 A1* | 3/2012 | Konishi et al. | 359/708 |
| 2013/0172677 A1* | 7/2013 | Kennedy et al. | 600/112 |

FOREIGN PATENT DOCUMENTS

| | | |
|---|---|---|
| JP | S64-46001 | 3/1989 |
| JP | 08-256976 | 10/1996 |
| JP | 11-249030 | 9/1999 |
| JP | 11-262467 | 9/1999 |
| JP | 2000-083252 | 3/2000 |
| JP | 2000-139821 | 5/2000 |
| JP | 2000-232957 | 8/2000 |
| JP | 2000-266979 | 9/2000 |
| JP | 2003-204934 | 7/2003 |
| JP | 2005-209967 | 8/2005 |
| JP | 2008-253789 A | 10/2008 |
| JP | 2010-069217 | 4/2010 |

* cited by examiner

Endoscope

Image Pickup System

IMAGE PICKUP UNIT AND ENDOSCOPE DISTAL END PORTION INCLUDING THE IMAGE PICKUP UNIT

CROSS REFERENCE TO RELATED APPLICATION

This application is a continuation application of PCT/JP2011/069081 filed on Aug. 24, 2011 and claims benefit of Japanese Application No. 2010-203400 filed in Japan on Sep. 10, 2010, the entire contents of which are incorporated herein by this reference.

BACKGROUND OF INVENTION

1. Field of the Invention

The present invention relates to an image pickup unit including an image pickup optical system and an image pickup device, and an endoscope distal end portion including the image pickup unit.

2. Description of the Related Art

Conventionally, image pickup apparatuses including a solid-state image pickup device (hereinafter simply referred to as image pickup device) such as CCD or CMOS that converts light entering a light-receiving section provided in a semiconductor substrate into electric signals to pick up an image of an object have been known.

The image pickup apparatuses are used together with image pickup optical systems in electronic endoscopes and electronic equipment such as camera-equipped mobile phones and digital cameras, as image pickup units.

Also, in recent years, for the image pickup apparatuses, wafer-level chip-size package (hereinafter referred to as WL-CSP)-type ones have been known.

In WL-CSP, a cover glass wafer is attached at wafer level to a sensor wafer in which a plurality of semiconductor chips each including an image sensor formed therein are formed, and then the wafer is separated into the individual semiconductor chips, whereby a plurality of image pickup apparatus packages are completed.

A configuration using such a WL-CSP-type image pickup apparatus in an image pickup unit is disclosed in Japanese Patent Application Laid-Open Publication No. 2005-209967.

Japanese Patent Application Laid-Open Publication No. 2005-209967 discloses a configuration in which an image pickup unit includes a WL-CSP-type image pickup apparatus with a cover glass attached to a light-receiving surface of an image pickup device via a bonding layer, and a lens holder, which is a barrel body that holds an image pickup optical system, and inside the lens holder, the image pickup apparatus is provided and held at the rear, in an optical axis direction of the image pickup optical system, of the image pickup optical system, the lens holder thus covers the image pickup device and an outer circumferential face of the cover glass and thereby shields the outer circumferential face of the cover glass from light and protects the image pickup device, and the image pickup optical system is positioned relative to the image pickup device in the optical axis direction and a width direction orthogonal to the optical axis direction.

SUMMARY OF THE INVENTION

An image pickup unit according to an aspect of the present invention includes: a barrel body that holds an image pickup optical system in an inner portion thereof; an image pickup device including a light-receiving section that receives light entering via the image pickup optical system, the image pickup device being positioned at a rear, in an optical axis direction of the image pickup optical system, of the image pickup optical system; a cover glass attached to a facing surface of the image pickup device, the facing surface facing the image pickup optical system; and a fitting portion formed in at least an outer circumferential face of the cover glass, the fitting portion allowing a rear end-side part in the optical axis direction of the barrel body to be fitted thereon, and the barrel body and the image pickup device are each formed to have a size allowing the barrel body and the image pickup device to have a same width in a width direction orthogonal to the optical axis direction when the rear end-side part of the barrel body is fitted on the fitting portion.

Also, in an endoscope distal end portion including an image pickup apparatus according to an aspect of the present invention, the image pickup unit according to the aspect is provided in an inner portion thereof.

DETAILED DESCRIPTION OF THE PREFERRED EMBODIMENT(S)

Embodiments of the present invention will be described below with reference to the drawings. Note that the drawings are schematic ones, a relationship between a thickness and a width of each member, and, e.g., ratios in thickness between the respective members are different from actual ones, and it should be understood that the drawings include parts with dimensional relationships and/or ratios mutually different among the drawings.

(First Embodiment)

Figure 1:
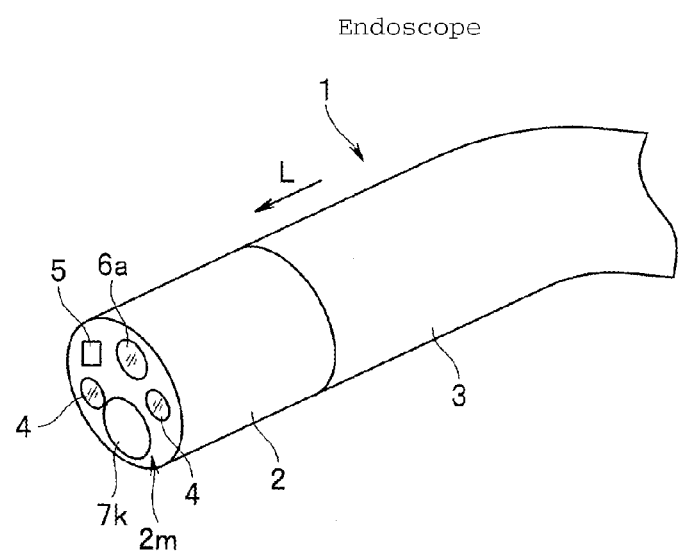
FIG. 1 is a partial perspective diagram illustrating a distal end side of an insertion portion of an endoscope in which an image pickup unit according to a first embodiment is provided inside a distal end portion of the insertion portion.
Figure 2:
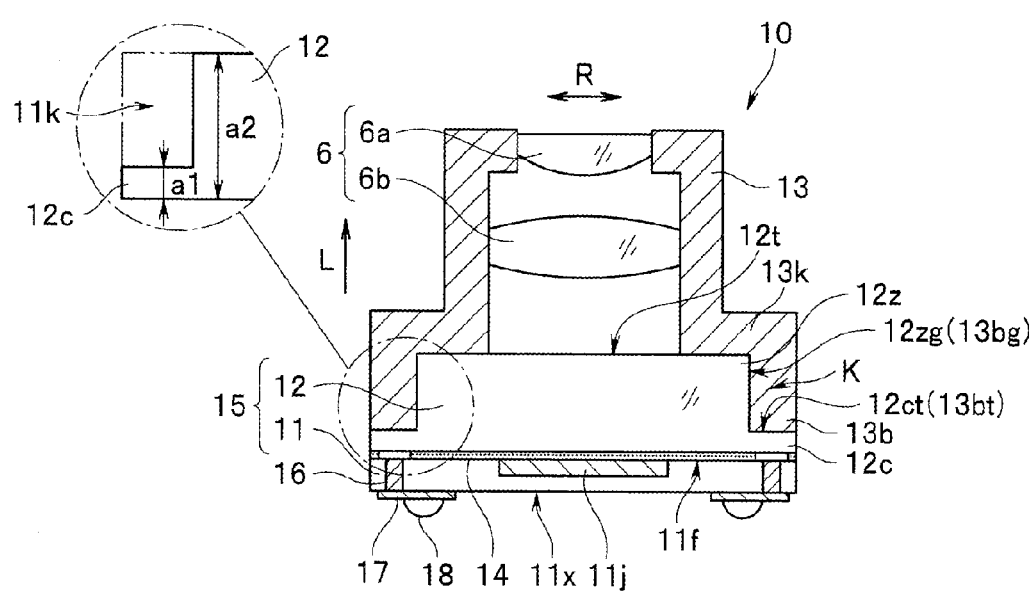
FIG. 2 is a partial cross-sectional diagram schematically illustrating a configuration of the image pickup unit provided inside the distal end portion in FIG. 1.

FIG. 1 is a partial perspective diagram illustrating a distal end side of an insertion portion of an endoscope in which an image pickup unit according to the present embodiment is provided inside a distal end portion of the insertion portion, and FIG. 2 is a partial cross-sectional diagram schematically illustrating a configuration of the image pickup unit provided inside the distal end portion in FIG. 1.

As illustrated in FIG. 1, at a distal end face 2m of a distal end portion 2 positioned on the distal end side in an optical axis direction L of a later-described lens 6 (hereinafter simply referred to as the distal end side) of an insertion portion 3 of an endoscope 1, an objective lens 6a for observing a site to be examined, for example, two illumination lenses 4 that illuminate the site to be examined, an air/water feeding nozzle 5 that supplies a fluid to a surface of the objective lens 6a to remove dirt on the surface of the objective lens 6a, and a distal end opening 7k of a non-illustrated channel provided inside the insertion portion 3, the channel being used when a treatment instrument is supplied to the site to be examined or a liquid or a solid positioned at the site to be examined is sucked. Note that the count of the illumination lenses 4 is not limited to two.

Also, inside the distal end portion 2, an image pickup unit 10, which is illustrated in FIG. 2, is provided. More specifically, as illustrated in FIG. 2, the image pickup unit 10 includes a lens holder 13, which is a barrel body that holds the lens 6, which is an image pickup optical system, on the distal end side of an inner portion thereof. The lens holder 13 is formed of, for example, a metal by, e.g., molding or machining.

Furthermore, although FIG. 2 indicates an example in which the lens 6 includes two lenses, i.e., an objective lens 6a, and a lens 6b positioned at the rear in the optical axis direction L (hereinafter simply referred to as the rear) of the objective lens 6a, the lens 6 may include one lens or a plurality of lenses, e.g., three or more lenses.

Furthermore, the lens holder 13 includes a shape flexed in a crank shape at a position partway in the optical axis direction L. In other words, the lens holder 13 includes a crank-shaped part 13k at the position partway in the optical axis direction.

An image pickup device 11 including a light-receiving section 11j that receives light entering via the lens 6 is provided at the rear of the lens 6.

A known cover glass 12 that protects a light-receiving surface of the light-receiving section 11j is attached to a facing surface 11f of the image pickup device 11, the facing surface 11f facing the lens 6, via an adhesive layer 14. The cover glass 12 is held by the lens holder 13 inside the lens holder 13.

The cover glass 12 has a function that supports the image pickup device 11, which is formed to be thin, to prevent mechanical deformation and/or breakage of the image pickup device 11 in addition to protecting the light-receiving surface of the light-receiving section 11j. The image pickup device 11 and the cover glass 12 provide a WL-CSP-type image pickup apparatus 15.

Also, in an area of the image pickup device 11 excluding the light-receiving section 11j in a planar view from the facing surface 11f side, through-wirings 16 extending from the facing surface 11f to a surface 11x opposite to the facing surface 11f are formed.

Also, on the surface 11x of the image pickup device 11, electrode pads 17 electrically connected to the through-wirings 16 are formed and electrodes 18 such as solder balls are electrically connected to the electrode pads 17.

An attachment part 12c of the cover glass 12, the attachment part 12c being attached to the facing surface 11f of the image pickup device 11, is formed so as to have a width equal to that of the image pickup device 11 in a width direction R of the image pickup device 11 orthogonal to the optical axis direction L.

Note that a thickness a1 in the optical axis direction L of the attachment part 12c is no less than ⅕ and no more than ½ of a thickness a2 in the optical axis direction L of the entire cover glass 12.

This is because if the attachment part 12c is overly thin, the problem of a decrease in mechanical strength of the attachment part 12c occurs, and conversely if the attachment part 12c is overly thick, the problem of a decrease in capability of shielding the light-receiving section 11j from light, which is provided by a later-described rear end-side part 13b of the lens holder 13, occurs.

Furthermore, a front part 12z positioned at the front in the optical axis direction L (hereinafter simply referred to as the front) of the attachment part 12c of the cover glass 12 is formed so as to have a width smaller than that of the attachment part 12c in the width direction R.

More specifically, the front part 12z is formed so as to have a width larger than a width of the light-receiving section 11j of the image pickup device 11 and have a width smaller than that of the image pickup device 11.

Consequently, at an outer circumferential face of the cover glass 12, a stepped portion is formed by a difference in size between the width of the attachment part 12c and the width of the front part 12z, and the stepped portion provides a fitting portion K having a rectangular shape in a cross-section.

Note that the rear end-side part of the lens holder 13 at the rear of the crank-shaped part 13k is fitted on the fitting portion K.

The rear end-side part 13b has a function that shields the light-receiving section 11j of the image pickup device 11 from unwanted light entering from the outside of the lens holder 13.

The fitting portion K is formed in a space having a shape that corresponds in size and shape to the rear end-side part 13b of the lens holder 13. More specifically, the fitting portion K is the same as the rear end-side part 13b of the lens holder 13 in length in the optical axis direction L and width in the width direction R and has a shape that is the same as that of the rear end-side part 13b of the lens holder 13.

Consequently, a lower end face 13bt of the rear end-side part 13b fitted on the fitting portion K is in close contact with an upper face 12ct of the attachment part 12c, an inner circumferential face 13bg of the rear end-side part 13b is in close contact with an outer circumferential face 12zg of the front part 12z, and furthermore, the lens holder 13 fitted on the fitting portion K and the image pickup device 11 have a same width in the width direction R.

Note that the lower end face 13bt and the inner circumferential face 13bg are bonded and thereby fixed to the upper face 12ct and the outer circumferential face 12zg, respectively, using, for example, a thermal curing adhesive, a photo curing adhesive or a photo-assisted thermal curing adhesive.

Also, the outer circumferential face 12zg and the upper face 12ct may be painted in, for example, black to provide a configuration that shields the light-receiving section 11j of the image pickup device 11 from unwanted light entering from the outside of the lens holder 13 in addition to light shielding provided by the rear end-side part 13b of the lens holder 13.

Furthermore, an inner circumferential face of the crank-shaped part 13k of the lens holder 13 abuts against a front face 12t of the cover glass 12, the front face 12t facing the lens 6.

As a result of the abutment of the crank-shaped part 13k against the front face 12t and the fitting of the rear end-side part 13*b* of the lens holder 13 on the fitting portion K, that is, the abutment of the lower end face 13*bt* against the upper face 12*ct* and the abutment of the inner circumferential face 13*bg* against the outer circumferential face 12*zg*, the lens 6 is positioned relative to the image pickup device 11 in the optical axis direction K and the width direction R.

Figure 3A:
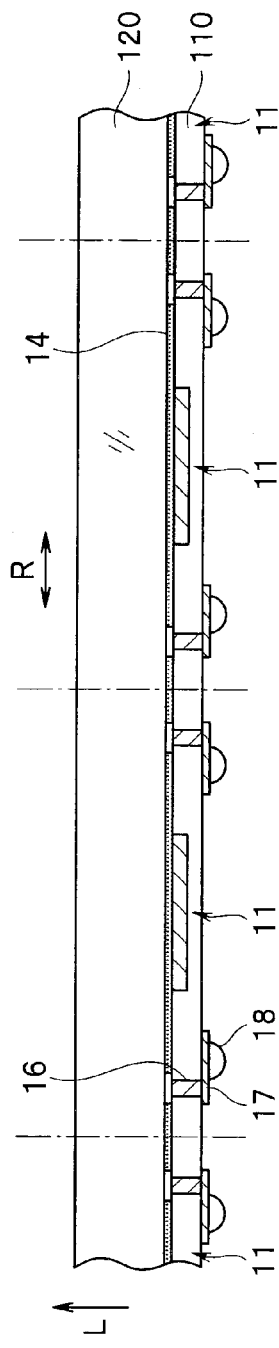
FIG. 3A is a diagram schematically illustrating a state in which a cover glass wafer is attached to a sensor wafer with a plurality of image pickup devices formed therein.
Figure 3B:
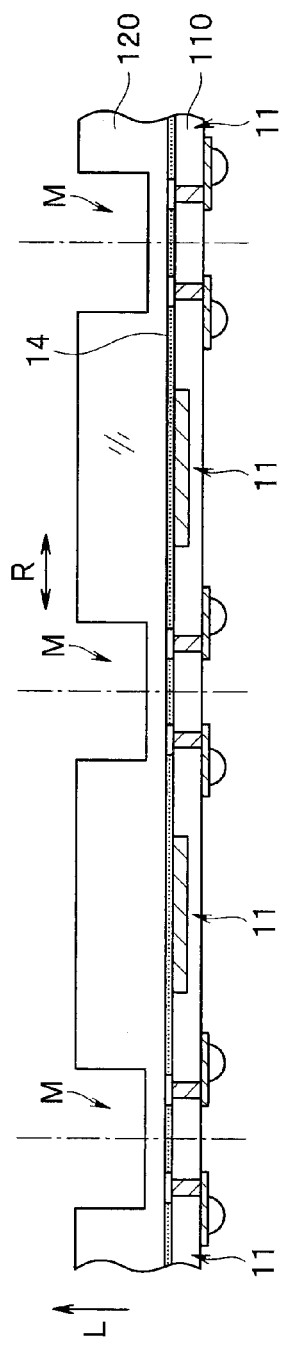
FIG. 3B is a diagram schematically illustrating a state in which the cover glass wafer in FIG. 3A has been subjected to half dicing.
Figure 3C:
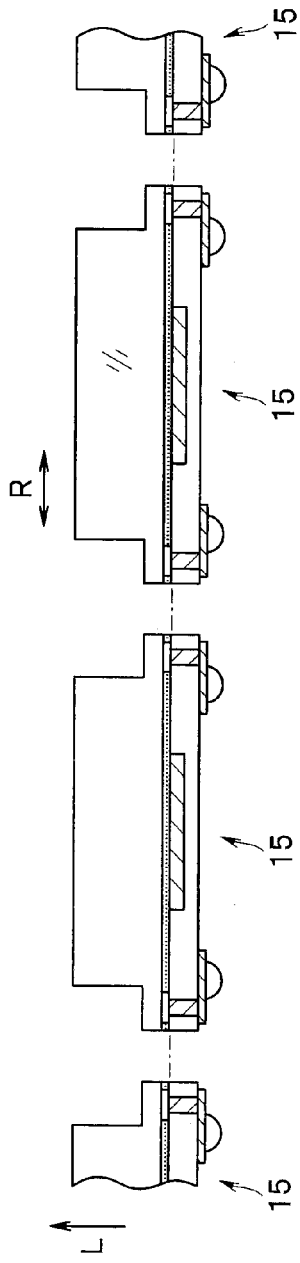
FIG. 3C is a diagram schematically illustrating a state in which the cover glass wafer and the sensor wafer in FIG. 3B have been subjected to full-cut dicing to form a plurality of image pickup apparatuses.

Next, a process for manufacturing the WL-CSP-type image pickup apparatus in FIG. 2 will be briefly described with reference to FIGS. 3A to 3C. FIGS. 3A to 3C are diagrams schematically illustrating a process for manufacturing the image pickup apparatus in FIG. 2: FIG. 3A is a diagram schematically illustrating a state in which a cover glass wafer has been attached to a sensor wafer with a plurality of image pickup device formed therein; FIG. 3B is a diagram schematically illustrating a state in which the cover glass wafer in FIG. 3A has been subjected to half-cut dicing; and FIG. 3C is a diagram schematically illustrating a state in which the cover glass wafer and the sensor wafer in FIG. 3B have been subjected to full-cut dicing to form a plurality of image pickup apparatuses.

First, as illustrated in FIG. 3A, a sensor wafer 110 with a plurality of image pickup devices 11 formed therein and with a cover glass wafer 120 attached thereto via the adhesive layer 14 is prepared.

In the sensor wafer 110, through-wirings 16 extending from a surface on the cover glass wafer 120 side of the sensor wafer 110 to a surface opposite to the surface of the sensor wafer 110, electrode pads 17 provided on the opposite surface of the sensor wafer 110 and electrically connected to the through-wirings 16, and electrodes 18 electrically connected to the electrode pads 17 are formed for each of the image pickup devices 11.

Next, as illustrated in FIG. 3B, positions corresponding to opposite end portions of each of the image pickup devices 11 in the cover glass wafer 120 are subjected to half-cut dicing using a dicing blade having a first width in the width direction R so as to have a thickness that is no less than ⅕ and no more than ½ of a thickness of the cover glass wafer 120, whereby grooves M are formed.

Formation of the grooves M may be conducted by not only dicing but etching. The first width is set to a value twice a width in the width direction R of the rear end-side part 13*b* of the lens holder 13 plus a second width, which will be described later.

Lastly, as illustrated in FIG. 3C, the positions where the grooves M of the cover glass wafer 120 are formed are subjected to full-cut dicing using a dicing blade having the second width smaller than the first width in the width direction R so that the cover glass wafer 120 and the sensor wafer 110 are cut through.

As a result, a plurality of image pickup apparatuses 15 are formed, and in a cover glass 12 of each of the image pickup apparatuses 15, an attachment part 12*c* resulting from the grooves M formed by half-cut dicing in FIG. 3B is formed, whereby a fitting portion K is formed.

As described above, the lens holder 13 is bonded and thereby fixed to each of the manufactured image pickup apparatuses 15, whereby image pickup units 10 are manufactured.

As described above, the present embodiment indicates that the fitting portion K formed so as to correspond in size and shape to the rear end-side part 13*b* of the lens holder 13 is formed in the cover glass 12, and the rear end-side part 13*b* is fitted on and bonded and thereby fixed to the fitting portion K.

Accordingly, even if the lens holder 13 is fixed to the image pickup apparatus 15, the lens holder 13 does not protrude outward in the width direction R from the image pickup device 11 as opposed to conventional techniques.

Therefore, it is possible to prevent an increase in width in the width direction R of an image pickup unit 10 due to the lens holder 13, and thus, the image pickup unit 10 can be downsized by a simple configuration. In other words, a distal end portion 2 of an insertion portion 3 of an endoscope 1 in which the image pickup unit 10 is provided can be downsized.

Furthermore, in the present embodiment, the rear end-side part 13*b* of the lens holder 13 is fitted on the fitting portion K and a crank-shaped part 13*k* of the lens holder 13 abuts against a front face 12*t* of the cover glass 12, whereby a lens 6 is positioned relative to the image pickup device 11 in the optical axis direction K and the width direction R.

Consequently, when the image pickup unit 10 is manufactured, mere fitting of the rear end-side part 13*b* on the fitting portion K makes the crank-shaped part 13*k* abut against the front face 12*t* of the cover glass 12, and automatically, the lens 6 is mechanically positioned relative to the image pickup device 11 in the optical axis direction K and the width direction R, eliminating the need to perform positioning using known positioning marks or perform positioning while performing observation via a camera, and thus, the lens 6 can easily be positioned relative to the image pickup device 11.

According to the above, the image pickup unit 10 including a configuration that includes the WL-CSP-type image pickup apparatus 15 held by the lens holder 13 and can be downsized in the width direction R, and an endoscope distal end portion 2 including the image pickup unit 10 can be provided.

Modifications are indicated below. The present embodiment indicates that a fitting portion K of a cover glass 12 is formed so as to have a rectangular shape in a cross-section by a stepped portion resulting from a difference in size in the width direction R between an attachment part 12*c* and a front part 12*z*.

The present invention is not limited thereto, and the cross-sectional shape of a fitting portion K may be, for example, a cross-sectional shape formed by a stair-like stepped portion in order to increase an area of an inner circumferential face 13*bg* of a rear end-side part 13*b* bonded to an outer circumferential face 12*zg* of a front part 12*z* or may be any shape as long as such shape provides mechanical strength, does not impair the capability of shielding a light-receiving section 11*j* from light and the rear end-side part 13*b* does not protrude outward in the width direction R from the image pickup device 11.

Figure 4:
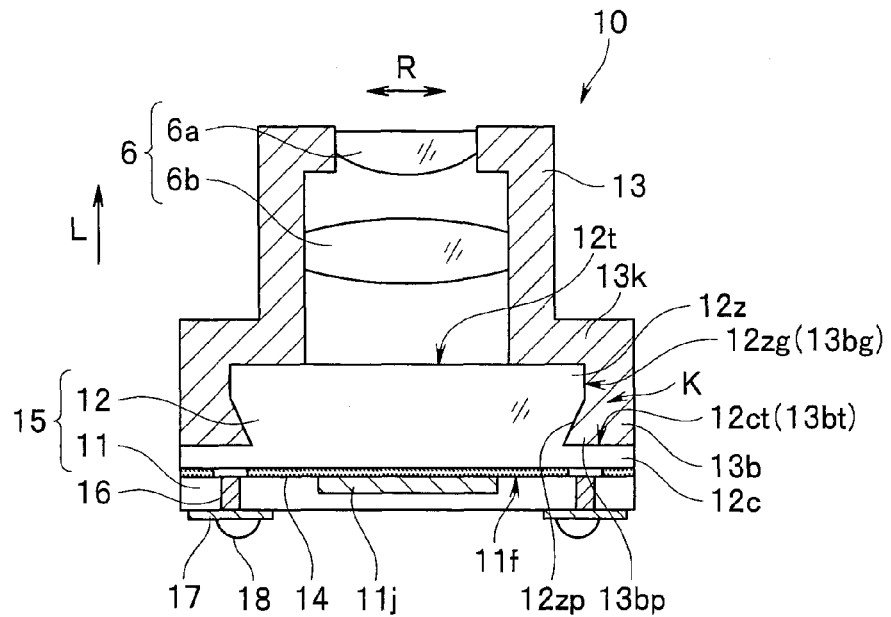
FIG. 4 is a partial cross-sectional diagram schematically illustrating a modification of the image pickup unit in which locking lugs provided at a rear end-side part of a lens holder in FIG. 2 are locked in locking grooves of a cover glass, whereby the lens holder is fixed to the cover glass.

Also, a modification will be indicated below with reference to FIG. 4. FIG. 4 is a partial cross-sectional diagram schematically illustrating a modification of the image pickup unit in FIG. 2 in which locking lugs provided at a rear end-side part of a lens holder are locked in locking grooves of a cover glass, whereby the lens holder is fixed to the cover glass.

As illustrated in FIG. 4, a configuration in which locking grooves 12*zp* each having an inversely tapered shape in a cross-section in an optical axis direction L are formed in at least parts of an outer circumferential face 12*zg* of a front part 12*z* of a cover glass 12 while locking lugs 13*bp* to be locked in the locking grooves 12*zp* are formed in at least parts of an inner circumferential face 13*bg* of a rear end-side part 13*b* of a lens holder 13, and locking of the locking lugs 13*bp* in the locking grooves 12*zp* makes the lens holder 13 be fitted on a fitting portion K of the cover glass 12 may be provided.

The locking grooves 12*zp* are formed by cutting a cover glass wafer 120 while a blade having, for example, a conical shape being rotated in the process of forming grooves M, which has been described above with reference to FIG. 3B.

Furthermore, if the locking groove 12*zp* is formed over the entire outer circumferential face 12*zg* of the front part 12*z* while the locking lug 13*bp* is formed over the entire inner circumferential face 13*bg* of the rear end-side part 13*b* of the lens holder 13, it is difficult to lock the locking lug 13*bp* in the locking groove 12*zp*.

Therefore, if the locking groove 12*zp* is formed at each of only two opposed positions of the outer circumferential face 12*zg* of the front part 12*z* while a rear end-side part 13*b* including the locking lug 13*bp* is formed at each of only two opposed portions of the lens holder 13, the locking lugs 13*bp* can be slidably fitted in the locking grooves 12*zp* in the width direction R, facilitating locking of the locking lugs 13*bp* in the locking grooves 12*zp*.

In this case, unwanted light may enter a light-receiving section 11*j* of an image pickup device 11 from a part with the rear end-side parts 13*b* not formed; however, this can be prevented by applying black paint to the outer circumferential face 12*zg* of the front part 12*z* of the cover glass 12 and an upper face 12*ct* of an attachment part 12*c* as described above.

Furthermore, where the fitting capability is ignored, the rear end-side part 13*b* may have the shape in the above-described first embodiment except the parts in which the locking lugs 13*bp* are formed.

According to the configuration described above, in addition to the effects of the above-described present embodiment, the lens holder 13 can be fixed to the fitting portion K of the cover glass 12 without bonding, enabling reduction in time required for curing of an adhesive, and thus, time for a process for manufacturing an image pickup unit 10 can be reduced.

(Second Embodiment)

Figure 5:
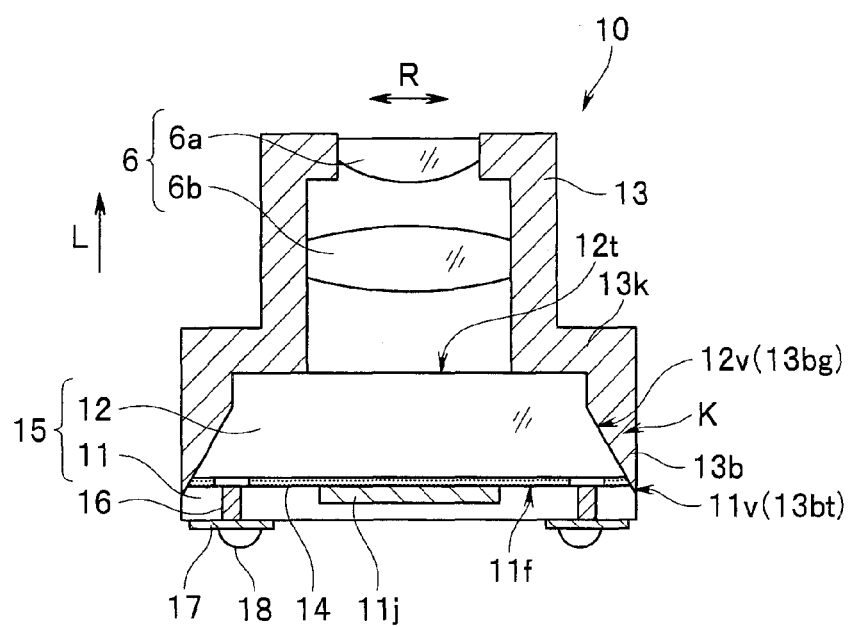
FIG. 5 is a partial cross-sectional diagram schematically illustrating a configuration of an image pickup unit according to a second embodiment.

FIG. 5 is a partial cross-sectional diagram schematically illustrating a configuration of an image pickup unit according to the present embodiment.

A configuration of the image pickup unit according to the second embodiment is different from that of the image pickup unit 10 according to the above-described first embodiment illustrated in FIG. 2 in that a fitting portion on which a rear end-side part of a lens holder is to be fitted is formed also in an outer circumferential face of an image pickup device. Therefore, a description will be provided only for this difference, and components similar to those of the first embodiment are provided with reference numerals that are the same as those of the first embodiment, and a description thereof will be omitted.

As illustrated in FIG. 5, in the present embodiment, an attachment part of a cover glass 12 attached to a facing surface 11*f* of an image pickup device 11 has a width smaller than that of the image pickup device 11 and a first tapered surface 12*v* is formed at an outer circumferential face of the cover glass 12 so that a width of the outer circumferential face of the cover glass 12 decreases forward.

Furthermore, a second tapered surface 11*v*, which is continuous with the first tapered surface 12*v*, is formed on the cover glass 12 side of an outer circumferential face of the image pickup device 11, and in the second tapered surface 11*v*, a width of the outer circumferential face of the second tapered surface 11*v* of the image pickup device 11 decreases forward. In other words, a tapered stepped portion is formed in the outer circumferential face of the image pickup device 11 and the outer circumferential face of the cover glass 12.

The first tapered surface 12*v* and the second tapered surface 11*v* are formed by cutting not only a cover glass wafer 120 but also a sensor wafer 110 to a predetermined depth using a V-shaped blade in the process of forming grooves M, which is illustrated in FIG. 3B.

As a result, a fitting portion K is formed in the outer circumferential faces of the cover glass 12 and the image pickup device 11 by the tapered stepped portion provided by the first tapered surface 12*v* and the second tapered surface 11*v*. In other words, in the present embodiment, the fitting portion K is formed also in the outer circumferential face of the image pickup device 11.

Here, the fitting portion K is formed so as to have a shape that corresponds in size and a shape to the rear end-side part 13*b* of the lens holder 13. In other words, an inner circumferential face 13*bg* of the rear end-side part 13*b* is also formed in a tapered shape.

Therefore, the inner circumferential face 13*bg* of the rear end-side part 13*b* fitted on the fitting portion K is bonded and thereby fixed in close contact to the first tapered surface 12*v* of the cover glass 12 and the second tapered surface 11*v* of the image pickup device 11, and as in the first embodiment, a width of the lens holder 13 is equal to that of the image pickup device 11 in the width direction R.

With such configuration, in addition to the effects of the first embodiment, a length of the rear end-side part 13*b* of the lens holder 13 is increased rearward, enabling completely shielding a light-receiving section 11*j* from light entering the light-receiving section 11*j* from the outside. In other words, the light shielding capability is enhanced compared to the first embodiment.

Furthermore, there is no need to form an attachment part 12*c*, which is thin in an optical axis direction L, in the cover glass 12 as opposed to the first embodiment, enabling enhancement in mechanical strength of the cover glass 12.

A substrate 30 (see FIG. 6) is electrically connected to electrodes 18 of an image pickup unit 10 indicated in the first embodiment and the second embodiment described above.

Figure 6:
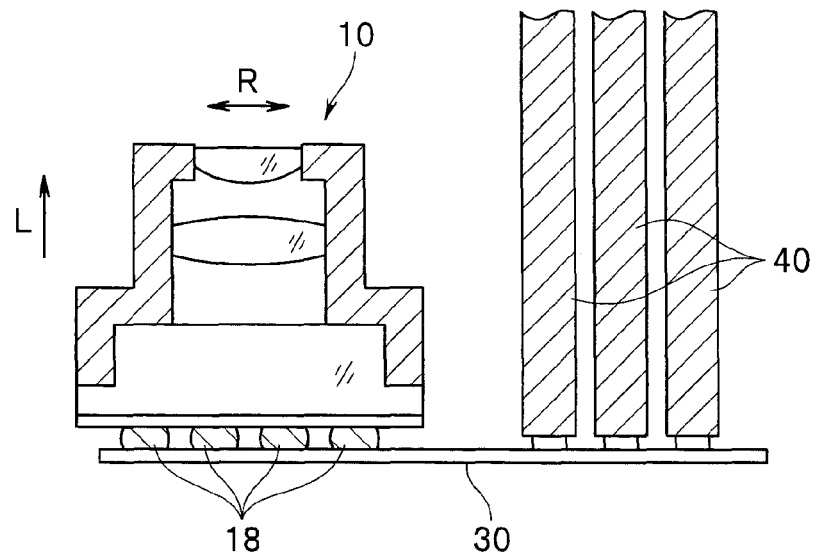
FIG. 6 is a partial cross-sectional diagram schematically illustrating a configuration in which a substrate is electrically connected to electrodes of the image pickup unit in FIG. 2.
Figure 7:
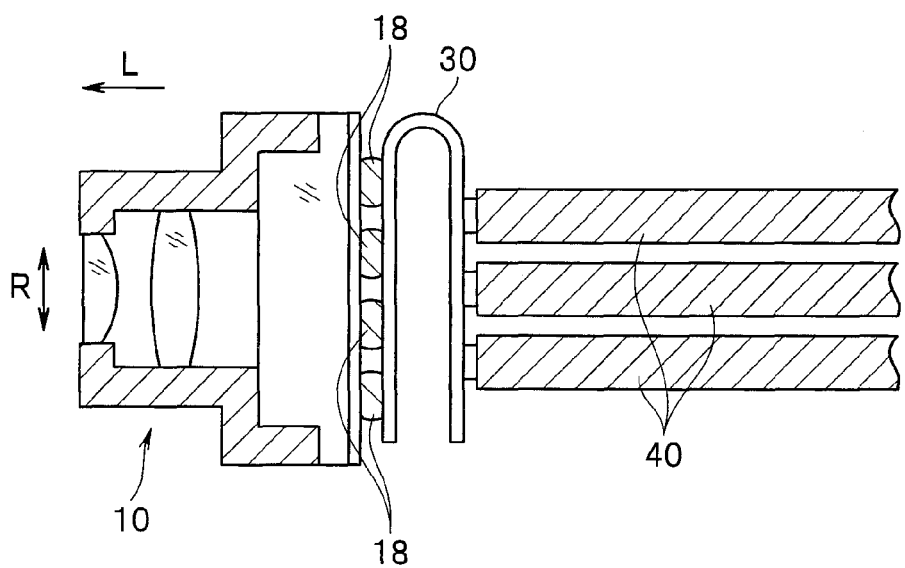
FIG. 7 is a partial cross-sectional diagram schematically illustrating a state in which the substrate in FIG. 6 has been bent.

A configuration in which a substrate is electrically connected to an image pickup unit will be indicated with reference to FIGS. 6 and 7, taking the image pickup unit indicated in the first embodiment as an example.

FIG. 6 is a partial cross-sectional diagram schematically illustrating a configuration in which a substrate is electrically connected to electrodes of the image pickup unit in FIG. 2, and FIG. 7 is a partial cross-sectional diagram schematically illustrating a state in which the substrate in FIG. 6 is bent.

Where an image pickup unit 10 is provided inside a distal end portion 2 of an insertion portion 3 of an endoscope 1, it is necessary to connect cables 40 for transmitting of data of an image picked up by the image pickup unit 10, to the image pickup unit 10.

Therefore, as illustrated in FIG. 6, the electrodes 18 such as solder balls electrically connected to electrode pads 17 provided on a surface 11*x* of an image pickup device 11 are electrically connected to non-illustrated image pickup device connection lands formed on a first surface of the substrate 30 such as, for example, a flexible substrate.

Furthermore, on the first surface of the substrate 30, non-illustrated lands for cable connection are formed at positions distant from the image pickup device connection lands in a width direction R, and the cables 40 with respective conductor wires having exposed end faces are electrically connected to the respective lands via connection means such as solder.

Connection of the cables 40 to the respective lands for cable connection is conducted by adjusting positions of the cables 40 while the substrate 30 is heated after the image pickup unit 10 is mounted on the substrate 30.

In this case, on a second surface of the substrate 30 opposite to the first surface, there are no components at positions facing the lands for cable connection, enabling heat to be reliably conveyed to the substrate 30, whereby highly-reliable connection of the cables 40 can be conducted.

Furthermore, as illustrated in FIG. 7, the substrate 30 is flexed at the rear of the image pickup unit 10, and the cables 40 are fixed to the electrodes 18 in such a manner that the cables extend out on the rear side of the image pickup unit 10.

In this case, the substrate 30 is flexed so as not to protrude from an outer shape of the image pickup unit 10 in a planar view from the image pickup unit 10 side, and thus, a decrease in width of the image pickup unit 10 can be achieved.

Although FIGS. 6 and 7 indicate the image pickup unit 10 according to the above-described first embodiment as an example, it should be understood that the image pickup unit according to the second embodiment may be employed.

Furthermore, the first and second embodiments described above indicate that the image pickup unit 10 is provided inside the distal end portion 2 of the insertion portion 3 of the endoscope 1; however, the present invention is not limited thereto, and it should be understood that the image pickup unit 10 may be provided in electronic equipment such as a mobile phone or a camera.

Furthermore, the above-described embodiments include inventions of various phases, and a proper combination of a plurality of elements disclosed herein enables extraction of various inventions. For example, even if several elements are deleted from all the elements indicated in the above embodiment, a resulting configuration with the elements deleted may be extracted as an invention as long as such configuration can solve the problem stated in the Problems to be Solved by the Invention section and provide effects described in the Advantages of the Invention.

What is claimed is:

1. An image pickup system comprising:
a lens holder;
an image pickup optical system that is secured by a portion of the lens holder;
an image pickup device comprising a first surface and a second surface, wherein the first surface is nearer the image pickup optical system than the second surface in an optical axis direction,
a light receiving sensor that receives light entering through the image pickup optical system, and
a cover glass attached to the first surface of the image pickup device, wherein the cover glass comprising a fitting portion of the cover glass in an outer circumferential face of the cover glass,
wherein the lens holder comprises a first end and a second end, the first end nearer the image pickup device than the second end in the optical axis direction, and
wherein at least a portion of the lens holder and the image pickup device are the same width or the image pickup device is a wider width than the lens holder, in a width direction orthogonal to the optical axis direction when the first end of the lens holder is fitted on the fitting portion of the cover glass.

2. The image pickup system according to claim 1, wherein a first portion of the cover glass has the same width as the image pickup device in the width direction and a second portion of the cover glass has a width smaller than that of the first portion of the cover glass, wherein the second portion of the cover glass is nearer the image pickup optical system than the first portion of the cover glass in the optical axis direction.

3. The image pickup system according to claim 2, wherein a thickness in the optical axis direction of the first portion of the cover glass is no less than ⅕ and no more than ½ of a combined thickness in the optical axis direction of the first portion of the cover glass and the second portion of the cover glass.

4. The image pickup system according to claim 2
wherein the lens holder comprises a rear portion of the lens holder and a front portion of the lens holder, the front portion of the lens holder is nearer the image pickup optical system than the rear portion of the lens holder in the optical axis direction, the rear portion of the lens holder comprising a locking lug,
wherein the second portion of the cover glass comprises a rear portion of the cover glass and a front portion of the cover glass, the front portion of the cover glass is nearer the image pickup optical system than the rear portion of the cover glass in the optical axis direction, the rear portion of the cover glass comprising a locking groove in which the locking lug is configured to be secured at the outer circumferential face of the rear portion of the cover glass; and
wherein the locking lug is secured by the locking groove.

5. The image pickup system according to claim 1, wherein a fitting portion of the image pickup device is in an outer circumferential face of the image pickup device.

6. The image pickup system according to claim 5,
wherein the cover glass has a width smaller than that of the image pickup device in the width direction orthogonal to the optical axis direction, and a first tapered surface of the cover glass decreases forward in the optical axis direction in a width of the outer circumferential face;
wherein the image pickup device comprises a second tapered surface in which the width of the outer circumferential face decreases forward in the optical axis direction, the second tapered surface is configured to contact the first tapered surface.

7. The image pickup system according to claim 1, wherein the first end of the lens holder is adhered to the fitting portion.

8. The image pickup system according to claim 1,
wherein the lens holder comprises a crank-shaped part in the first end of the lens holder, the cover glass comprising a front face and a rear face, the front face is nearer the image pickup optical system than the rear face in the optical axis direction, the crank-shaped part abutting the front face of the cover glass; and
wherein the fitting portion of the cover glass is configured to be secured by the first end of the lens holder and the image pickup optical system is aligned with the image pickup device in the optical axis direction and the width direction.

9. An endoscope distal end portion comprising an image pickup system according to claim 1 in an inner portion of the endoscope distal end portion.

* * * * *